United States Patent [19]

Weiss et al.

[11] Patent Number: 5,470,710
[45] Date of Patent: Nov. 28, 1995

[54] AUTOMATED HYBRIDIZATION/IMAGING DEVICE FOR FLUORESCENT MULTIPLEX DNA SEQUENCING

[75] Inventors: Robert B. Weiss; Alvin W. Kimball; Raymond F. Gesteland; F. Mark Ferguson, all of Salt Lake City; Diane M. Dunn, West Valley City; Leonard J. Di Sera; Joshua L. Cherry, both of Salt Lake City, all of Utah

[73] Assignee: University of Utah, Salt Lake City, Utah

[21] Appl. No.: 141,234

[22] Filed: Oct. 22, 1993

[51] Int. Cl.⁶ .................................................. C12Q 1/68
[52] U.S. Cl. ............................ 435/6; 435/7.1; 435/7.5; 435/7.9
[58] Field of Search ........................... 435/7.5, 6, 7.1, 435/7.72, 7.9, 7.92, 7.95, 21, 91.1, 91.5; 250/461.2

[56] References Cited

U.S. PATENT DOCUMENTS 5,112,736  5/1992  Caldwell et al. .................... 435/6

OTHER PUBLICATIONS

Richterich et al. (1989) Bio Techniques, vol. 7, pp. 52–59.
Cano et al. (1992) Bio Techniques, vol. 12, pp. 264–268.
Kostichka et al. (1992) Bio/Technology, vol. 10, pp. 78–81.
Holtke et al. (1990) Nucleic Acids Research, vol. 18, pp. 5843–5851.

Primary Examiner—Mindy B. Fleisher
Assistant Examiner—Philip W. Carter
Attorney, Agent, or Firm—Thorpe North & Western

[57] ABSTRACT

A method is disclosed for automated multiplex sequencing of DNA with an integrated automated imaging hybridization chamber system. This system comprises an hybridization chamber device for mounting a membrane containing size-fractionated multiplex sequencing reaction products, apparatus for fluid delivery to the chamber device, imaging apparatus for light delivery to the membrane and image recording of fluorescence emanating from the membrane while in the chamber device, and programmable controller apparatus for controlling operation of the system. The multiplex reaction products are hybridized with a probe, then an enzyme (such as alkaline phosphatase) is bound to a binding moiety on the probe, and a fluorogenic substrate (such as a benzothiazole derivative) is introduced into the chamber device by the fluid delivery apparatus. The enzyme converts the fluorogenic substrate into a fluorescent product which, when illuminated in the chamber device with a beam of light from the imaging apparatus, excites fluorescence of the fluorescent product to produce a pattern of hybridization. The pattern of hybridization is imaged by a CCD camera component of the imaging apparatus to obtain a series of digital signals. These signals are converted by the controller apparatus into a string of nucleotides corresponding to the nucleotide sequence an automated sequence reader. The method and apparatus are also applicable to other membrane-based applications such as colony and plaque hybridization and Southern, Northern, and Western blots.

10 Claims, 8 Drawing Sheets

AUTOMATED HYBRIDIZATION/IMAGING DEVICE FOR FLUORESCENT MULTIPLEX DNA SEQUENCING

This invention was made with government support under Grant No. DE-FG02-88ER60700 awarded by the U.S. Department of Energy and Grant Nos. R01-HG00517-02 and P30-HG00199-03 awarded by the National Center for Human Genome Research of the National Institutes of Health. The government has certain rights in the invention.

BACKGROUND OF THE INVENTION

This invention relates generally to the field of nucleic acid hybridization on membranes. More particularly, this invention relates to a method for automated multiplex sequencing of DNA.

Large scale nucleotide sequencing initiatives, such as a project to sequence the human genome, have created a need for increased efficiency and productivity. J. Watson, 248 Science 44 (1990). Automation of the various steps involved in sequencing is one area in which gains in efficiency and productivity are being made.

Multiplex sequencing, one scheme for reducing the number of sequencing reactions and electrophoresis steps, involves the processing of a mixture of sequencing templates followed by sequential hybridization with selected probes. G. Church & S. Kieffer-Higgins, 240 Science 185 (1988); U.S. Pat. No. 4,942,124. In this method, many sequencing templates, each carrying a short known sequence or tag, are processed together. A single DNA preparation yields a mixture of templates. Sequencing reactions are performed on the mixture in the absence of any label, and the mixed reaction products are fractionated by electrophoresis, transferred to a membrane, and probed sequentially by hybridization with labeled oligonucleotides specific for each tag. Each hybridization step reveals the nucleotide sequence of one component of the template mixture. Between hybridizations the labeled probe is removed to permit the next hybridization without interference from the previous probe. The advantages of multiplex sequencing come from the parallel processing of template preparations and sequencing reactions, and the simultaneous electrophoresis of mixtures of templates. Multiplex sequencing can reduce the time, effort, and resources needed for these steps by about a factor of the number of different sequencing templates in the mixture.

The savings made in sequencing reactions and electrophoresis by multiplex sequencing are offset to some extent, however, by new steps that are unnecessary in conventional sequencing protocols. Hybridization of the membrane is an added step that is repeated with each specific probe. Fortunately, however, the hybridization process is automatable. P. Richterich et al., 7 Bio/Techniques 52 (1989). A remaining problem is the acquisition of sequence data in electronic form. Automated sequencing machines are available that detect fluorescently labeled sequencing products as they migrate through a gel. The data acquired in this way are then interpreted by an algorithm that yields a called sequence. Most large-scale sequencing efforts have turned toward such machines as the only way of obtaining sufficient efficiency.

Conventionally, hybridization probes have been labeled with radioisotopes. Although radioactive probes can detect minute quantities of DNA, they are hazardous and unstable, and high-resolution direct imaging of radioactive signals is not straight-forward. Non-radioactive methods of DNA detection have been developed in recent years. The most sensitive methods involve enzymatic conversion of substrates to colored, J. Leary et al., 80 Proc. Nat'l Acad. Sci. USA 4045 (1983), or chemiluminescent products, J. Voyta et al., 34 J. Clin. Chem. 1157 (1988); A. Schaap et al., 28 Tetrahedron Lett. 1159 (1987); I. Bronstein et al. 180 Anal. Biochem. 95 (1989). In this approach, an enzyme is linked to a probe, and an enzyme substrate that yields a colored or chemiluminescent product is applied to the membrane. After the enzyme acts on the substrate, the result is a pattern of color or light corresponding to the pattern of the target DNA on the membrane. Although colorimetric detection of sequence ladders has been achieved, P. Richterich et al, 7 Bio/Techniques 52 (1989), the inability to remove the colored product from the membrane precludes its use for sequential probing.

As currently practiced, automated DNA sequencing makes use of fluorescent labels for DNA detection. L. Smith et al., 321 Nature 674 (1986); W. Ansorge et al., 15 Nucleic Acids Res. 4593 (1987); J. Prober et al., 238 Science 336 (1987). In these methods fluorescence detection occurs while the DNA is in the gel. Under such conditions, a single fluorescent moiety per DNA molecule is sufficient for detection. Attempts at fluorescent detection in multiplex sequencing revealed a grossly inadequate limit of detection for DNA sequencing purposes. A. Karger et al., 206 Proc. SPIE 78 (1990). Background fluorescence from most membranes adds large quantities of noise, T. Chu et al., 13 Electrophoresis 105 (1992); U.S. Pat. No. 5,112,736, so that a much more intense signal is required to achieve an adequate signal-to-noise ratio than is required in a gel. Low fluorescence membranes, such as amine derivatized polypropylene (e.g., U.S. Pat. No. 5,112,736), are known, however such low flourescence membranes are restricted by a limit of detection about 100-fold too high for multiplex sequencing and the membranes are more fragile than nylon membranes.

Chemiluminescent hybridization signals are typically imaged by exposure to X-ray film although other methods are known, such as with a CCD (charge-coupled device) camera. U.S. Pat. No. 5,162,654. However the light output from chemiluminescence is quite low. Although enzymatic turnover results in many chemiluminescent molecules per target DNA molecule, at most one photon is emitted for each product molecule produced and in practice there is only about 1 photon emitted per $10^4$ molecules. Due to the low level of light emitted, a sensitive, low-noise detector, such as a cryogenically cooled CCD, is required for imaging, and a long exposure time is needed. A fully automated system based on chemiluminescence could be constructed, but it would be expensive and slow.

In the most straightforward operational mode, a CCD image is acquired as a snapshot, analogous to the operation of a photographic camera. The major advantages of digital imaging, in particular fast visualization, high sensitivity, quantitative imaging, and computer readable format, have been well documented. E. Ribeiro et al., 194 Anal. Biochem. 174 (1991); P. Jackson et al., 9 Electrophoresis 330 (1988); P. Jackson, 270 Biochem. J. 705 (1990); K. Chan et al., 63 Anal. Chem. 746 (1991); M. Lanan et al., 31 Biopolymers 1095 (1991); M. Lanan et al., 64 Anal. Chem. 1967 (1992); A. Karger et al., 1206 Proc. SPIE 78 (1990); K. Misiura et al. 18 Nucleic Acids Res. 4345 (1990); D. Pollard-Knight et al., 185 Anal. Biochem. 84 (1990); Z. Boniszewski et al., 11 Electrophoresis 432 (1990). When compared to other methods of visualization, however, such as autoradiography using isotope labels and X-ray film, the most obvious limitation of CCD imaging lies in the dimensions of the sensor arrays most commonly used in analytical applications. Their limited size rules out the recording of high-resolution electropherograms on a single frame. The large number of bands that can be resolved by high-resolution electrophoretic methods far exceeds the number of bands that can be adequately sampled on arrays having 512 to 768 CCD elements along their long axis, such as those referenced above.

One solution to obtaining a CCD image with adequate sampling over the entire surface of sequencing electropherograms is by manually merging partially overlapping individual frames on a computer screen using an image analysis tool. P. Jackson, 270 *Biochem. J.* 705 (1990). However, this procedure is time consuming and labor intensive, and the quality of the resulting composite image is compromised by discontinuities.

Another solution would be to use larger CCD arrays. CCD arrays consisting of 2048 elements square are commercially available, although at prices that are often prohibitive for analytical applications. Considering that several thousand data points need to be collected when several hundred bands are being separated, even a state-of-the-art, 4-megapixel CCD area array will fall short of the most demanding requirements of high-resolution separations. DNA sequencing, for example, requires sampling capability for well above 500 bands on a single lane, translating into much more than 2048 data points.

Continuous data acquisition using an area CCD can be achieved by operating the CCD camera in Time Delay and Integration (TDI) mode. Line scan CCD cameras are also available, but TDI mode provides greater sensitivity than line scan. TDI operation adds the capability of continuous data acquisition independent of the array length. This has been shown for two high-speed, fluorescence DNA sequencing formats: capillary electrophoresis, A. Karger, et al., 18 *Nucleic Acids Res.* 4955 (1991), and ultrathin slab gels, A. Kostichka et al., 10 *Bio/Technology* 78 (1992). TDI mode has also been used to monitor migrating fluorescent bands in capillary electrophoresis along the length of the column with a CCD camera. J. Sweedler et al., 63 *Anal. Chem.* 496 (1991). A TDI system for fluorescence detection on membranes is needed for automation of multiplex sequencing.

The task of converting relative band positions into nucleotide sequence is conceptually simple, however, the 1–3% error rate of human readers indicates that reading is more complex in practice. Band amplitudes and positions vary due to enzyme behavior and other biochemical factors, and instrumentation and handling factors, such as uneven temperature distribution. Band positions as a function of fragment size typically follow either quasi-logarithmic or constant spacing rules, depending on the instrumentation, but spatial jitter and position anomalies can be large enough to superimpose adjacent bands. Interlane band amplitudes vary, and intralane band amplitudes change both locally and along the length of the lane. Across a given electrophoretic gel, bands change width and may be tilted or take on complex shapes. Automated sequence readers must be able to deal with all this variation.

OBJECTS AND SUMMARY OF THE INVENTION

It is an object of the present invention to provide a system and method for automated multiplex sequencing of DNA.

It is also an object of the invention to provide an apparatus for automatic hybridization and washing of sequencing membranes, detection and imaging of fluorescent signals, and producing a called sequence with existing software from sequence data on the sequencing membranes.

An additional object is to provide an apparatus capable of handling other membrane-based detection methods such as colony and plaque hybridizations; Southern, Northern, and Western blot procedures; multiplex genotyping of simple sequence repeats; sequencing and mapping by hybridization; and dot, slot, and allele-specific oligonucleotide blot techniques.

It is another object of the invention to provide a system and method for detecting DNA on sequencing membranes that is compatible with automated multiplex sequencing.

It is a further object of the invention to provide a system and method for imaging fluorescent signals on sequencing membranes that is compatible with automated multiplex sequencing and which is also applicable to other membrane-based detection methods.

Yet a different object is to provide a method for enzyme-linked fluorescent detection of membrane-bound nucleic acid.

These and other objects may be accomplished by a method for sequencing a nucleic acid specimen by automated multiplex sequencing comprising the steps of (a) preparing multiplex sequencing reaction products, (b) separating the sequencing products according to their size, (c) attaching the separated sequencing products to a membrane, (d) placing the membrane in a chamber device of an integrated automated imaging hybridization chamber system comprising an hybridization chamber device, means for fluid delivery to the chamber device, imaging means for light delivery to the membrane and image recording of fluorescence emanating from the membrane while in the chamber device, and controller means for controlling the operation of the system, (e) introducing a first oligonucleotide probe containing an enzyme binding moiety, the probe capable of specifically hybridizing with a tag sequence on the membrane-bound sequencing products, into the chamber device by the fluid delivery means and thereby hybridizing the probe to the fractionated products, (f) introducing an enzyme into the chamber device by the fluid delivery means and binding enzyme to the binding moiety on the first oligonucleotide probe, (g) introducing a fluorogenic substrate into the chamber device by the fluid delivery means and contacting the enzyme with the substrate so that the substrate is converted into a fluorescent product, (h) illuminating the fluorescent product in the chamber device with a beam of light from the imaging means to excite fluorescence of the fluorescent product and produce a pattern of hybridization that reflects the nucleotide sequence of the nucleic acid specimen, (i) imaging the hybridization pattern by the imaging means and storing the pattern of hybridization as digital signals, and (j) converting the digital signals by the controller means into a linear string of nucleotides corresponding to the nucleotide sequence of the nucleic acid specimen.

Another aspect of the invention is adding the additional steps of (k) removing the fluorescent product from the membrane by introducing an appropriate wash solution into the chamber compartment by the fluid delivery means, (1) introducing a second oligonucleotide probe, containing a binding moiety to which an enzyme may be bound and which is able to hybridize specifically with a tag sequence different than the tag sequence of step (e), into the chamber device by the fluid delivery means and hybridizing the second probe to the fractionated products, introducing an enzyme into said chamber device by the fluid delivery means and binding the enzyme to the binding moiety on the second oligonucleotide probe, and repeating steps (g) through (j).

Another aspect of the invention is providing a fluorogenic substrate that is converted into a fluorescent product by an enzyme, wherein enzyme turnover produces many copies of the fluorescent product, the fluorescent product produces a clear pattern of hybridization with the support-bound nucleic acid, and the fluorescent product is easily removed for subsequent rounds of hybridization. Illustrative of suitable fluorogenic substrates is the benzothiazole derivative, 2'-(2-benzothiazolyl)-6'-hydroxybenzothiazole phosphate (BBTP). Alkaline phosphatase catalyzes the conversion of BBTP into the fluorescent product BBT. BBT does not diffuse on nylon membranes thus providing a sharp fluorescent image of membrane-bound DNA when illuminated with a wavelength of light that excites fluorescence. BBT is easily removed from the membrane by washing in detergent so that subsequent hybridizations can be performed on the same membrane.

Another aspect of the invention is an automated imaging hybridization chamber for automatic hybridization and imaging of multiplex sequencing membranes. The automated imaging hybridization chamber comprises a pair of concentric nested horizontal cylinders, i.e., a sealed inner cylinder that is rotatable about an axis and a sealable stationary outer cylinder having a light transparent window and entry means through which the inner cylinder may be accessed. The outer surface of the inner cylinder, containing means for attaching the sequencing membrane thereto, is spaced apart from the inner surface of the outer cylinder thereby forming an enclosed chamber compartment, the lower portion of which may be employed for receiving fluids (referred to as a "fluid puddle") used in the hybridization process. The portion of the chamber compartment above the fluid is an air space through which the membrane may be visualized and subjected to light through the transparent window in the outer cylinder. The inner cylinder is rotatable on an axle and is coupled to a stepper motor through gears and a toothed belt for causing the inner cylinder to rotate. The underside of the outer cylinder contains a plurality of valved ports extending through the cylinder wall through which fluids may be injected and removed from the chamber without cross contamination of the fluids. Each port is either coupled to a fluid delivery module for storing and delivering the fluids to the chamber compartment or to drain means for removing fluid from the chamber compartment. One type of fluid delivery module includes a large capacity reservoir and a metering pump. Optionally, a batch heater is included for heating the fluids before they are inserted into the chamber. A second type of fluid delivery module includes a probe reservoir, a large capacity reservoir, and a dual headed peristaltic pump for mixing probes with other solutions and delivering the fluid mixture to the chamber. Probe reservoirs can also be of the non-mixing type. Optionally, a refrigeration unit may be included to chill probe or other solutions.

Another aspect of the invention includes an imaging apparatus for imaging the pattern of hybridization on the membrane while the membrane is within the chamber. The outer cylinder advantageously includes a window of optically transparent material through which visible light may pass. A light source appropriately positioned outside the outer cylinder relative to the transparent window illuminates the membrane at a wavelength of light for exciting fluorescence of the fluorescent product on the membrane. A lens can be used to widen the distribution of the beam of light. A filter removes unwanted wavelengths of light. A CCD camera also appropriately positioned outside the outer cylinder relative to the transparent window operating in Time Delay and Integration mode records an image of the pattern of hybridization produced by the fluorescence. A filter removes interfering wavelengths of light from background sources. To generate an image, the membrane, which is mounted on the inner chamber, is moved relative to the CCD camera. This movement is caused by rotation of the inner chamber by the stepper motor and is synchronized with CCD pixel shifts in the camera. The image is stored electronically.

The above provides an overall summary of a preferred embodiment to a complete and integrated system and method for multiplex DNA sequencing. However, portions of the integrated system and/or method taken separately or combined may be utilized in other embodiments. For example, hybridization means other than the automated chamber may be utilized in a multiplexing operation. Also, membrane bound nucleic acids may be detected by enzyme-linked fluorescence without using the specific hybridization chamber or the specific imaging means disclosed. Further, the disclosed hybridization chamber can be used without the disclosed imaging means and/or fluorescence system.

DETAILED DESCRIPTION OF THE INVENTION

Before the present method of automated multiplex nucleotide sequencing is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and their equivalents.

As used herein, "membrane" includes thin films composed of nylon, nitrocellulose, polypropylene, and the like, as well as their functional equivalents now known in the art or later developed. Also, other solid supports to which a nucleic acid may be bound, hybridized and detected by enzyme-linked fluorescence is considered a functional membrane equivalent even if not in the form of a thin film.

As used herein, "macromolecule" means a nucleic acid or protein or their functional equivalents. For example, nucleic acid is intended to include naturally occurring and synthetic oligonucleotides and polynucleotides regardless of whether they contain ribose, deoxyribose, or dideoxyribose sugars or a combination thereof, and regardless of whether they are single stranded, double stranded, or a combination thereof. Protein is intended to include oligopeptides and polypeptides, whether naturally occurring or synthetic.

Enzyme-Linked Fluorescent Detection of DNA

One way of increasing fluorescent light output is to make use of enzymatic turnover to yield many fluorescent molecules per target DNA molecule. Fluorogenic substrates, compounds exhibiting low fluorescence which yield highly fluorescent products when acted upon by an enzyme, are available for several enzymes. Each molecule of enzyme can catalyze the production of many fluorescent molecules. The following fluorogenic substrates for calf intestinal alkaline phosphatase were tested as agents for visualization of probed DNA sequence ladders on nylon membranes: β-methylumbelliferyl phosphate (MUFP), 5-methyl fluorescein phosphate (5MFP), and 2'-(2-benzothiazolyl)-6'-hydroxybenzothiazole phosphate (BBTP). MUFP is commonly used in fluorescent assays for alkaline phosphatase, whereas 5MFP is a weakly fluorescent compound that, when hydrolyzed, yields the methyl ether of the common fluorophore, fluorescein. BBTP, also known as "ATTOPHOS," R. Cano et al., 12 Bio/Techniques 264 (1992), is hydrolyzed by alkaline phosphatase to the highly fluorescent 2'- (2-benzothiazolyl) -6'-hydroxybenzothiazole (BBT). R. Klem & W. Marvin, *Preparation and Use of Fluorescent Benzothiazole Derivatives*, PCT WO 90/00618 (Jan. 25, 1990). While BBTD is the preferred substrate thus far considered, the invention is not limited to any particular chemical structure for a fluoregenic substrate. Any substrate which does not diffuse on the membrane of choice thereby providing a sharp fluorescent image of membrane-bound DNA when illuminated with a wavelength of light that excites fluorescence is suitable. Preferably the substrate will also be is easily removed from the membrane by washing in detergent so that subsequent hybridizations can be performed on the same membrane.

Example 1

A sequencing reaction was prepared using the dideoxynucleotide chain termination method of F. Sanger et al., 74 *Proc. Nat'l Acad. Sci USA* 5464 (1977), with 1 pmol of M13mp19 template DNA and T7 DNA polymerase. Single-stranded template DNA was prepared from M13mp19 phage grown and purified from *E. coli* 71–18 using polyethylene glycol/NaCl precipitation followed by phenol/chloroform extraction and ethanol precipitation. J. Messing et al., 9 *Nucleic Acids Res.* 309 (1981). For sequencing, 2 pmol of "universal" sequencing primer and 1 pmol of template DNA were annealed in a 10 μl volume containing 4 mM $MnCl_2$, 80 mM Tris. HCl, pH 7.6, 30 mM sodium isocitrate, 10 mM dithiothreitol, and 0.1 μM of each of the four deoxynucleoside triphosphates. Annealing was at 65° C. for two minutes, then at 37° C. for 15 minutes, before addition of 2 units of T7 DNA polymerase (Sequenase 2.0, U.S. Biochemicals). After 1 minute at room temperature, 2.5 μl of this mixture was placed into each of four microtiter wells containing 2.5 μl of the appropriate deoxy(dNTP) and dideoxy-(ddNTP) nucleotides. All d/ddNTP mixtures contained 300 μM dNTP and 1 μM of the appropriate ddNTP. The reaction was incubated at 37° C. for 8 minutes and terminated by the addition of 6 μl of stop solution containing 98% formamide, 0.1% xylene cyanol, and 0.1% bromphenol blue, and heating on a boiling water bath for 3 minutes.

Reaction products were loaded in three sets of four lanes each (corresponding to the four deoxynucleotides A, C, G, and T), and were fractionated and then transferred to a nylon membrane. A 4% acrylamide slab gel (Long Ranger Gel Solution, AT BioChem Inc., Malvern, Pa.) containing 1×TBE buffer (89 mM Tris base, 89 mM boric acid, 2 mM EDTA, pH 8.3) was poured between 80 cm×35 cm glass plates using a 0.2 mm to 0.1 mm reverse wedge spacer. Gels were prerun at 50 V/cm, then 0.75 μl of sequence reaction was loaded per lane. DNA fragments were fractionated at 50 V/cm with passive thermostating provided by aluminum plates clamped to both glass surfaces. The electrophoresis system was a direct transfer apparatus, F. Pohl & S. Beck, 155 *Meth. Enzymol.* 250 (R. Wu ed., 1987) and hereby incorporated by reference, containing a custom stepper motor and controls, that pulls the membrane at a constant rate perpendicular to the bottom edge of the glass plates, thus, transferring the DNA fragments to the membrane. Conventional methods of transferring DNA from gels to membranes, such as electroblotting as described in U.S. Pat. No. 5,112,736, would also be adequate. After electrophoresis and transfer, the membrane was removed from the apparatus, rehydrated in 40 mM sodium phosphate buffer, pH 7.6, and irradiated with a total of 225 $mJ/cm^2$ of UV light to cross link the DNA fragments to the nylon membrane. Unbound DNA was removed by washing the membrane in PBS (40 mM sodium phosphate, pH 7.6, 150 mM NaCl), 5% SDS, and then the membranes were stored in the same buffer.

Example 2

The membrane from Example 1 was placed in an automated imaging hybridization chamber, to be described momentarily, where it was probed with a biotinylated oligonucleotide complementary to positions 80 to 110 of the ladder, and then treated with a streptavidin-alkaline phosphatase conjugate. Complete cycle time was 4.5 hours. The rotation of the inner cylinder within the hybridization chamber device was set to sweep a bead of fluid across the convex surface of the membrane, by movement of the membrane through the fluid, at approximately 20 second intervals. Hybridization volumes were 50 ml total, and wash volumes were 100 ml each. Unbound probe was removed by 8 washes with phosphate buffered saline (PBS) containing 5% SDS. Then a 1/5000 dilution of streptavidin-alkaline phosphatase (Boehringer Mannheim, 1000 U/ml) was applied in a total volume of 40 ml of PBS, 5% SDS. The enzyme conjugate was allowed to bind for 45 minutes. Then, unbound conjugate was removed by 1 wash with PBS, 5% SDS; 1 wash with PBS, 1% SDS; 3 washes with PBS; and 3 washes with 0.1M diethanolamine, pH 10.0, 1 mM $MgCl_2$, 0.01% sodium azide.

Example 3

The membrane from Example 2 was cut so that each of the three substrates could be applied to a sequencing ladder. The enzymatic reaction was started by addition of 1 ml of a fluorogenic alkaline phosphatase substrate for every 300 $cm^2$ of membrane. The stock solutions were: MUFP-50 µg/ml in 0.1M diethanolamine, pH 10; 5MFP-50 µg/ml in 0.1M diethanolamine, pH 10; and BBTP-600 µg/ml in 2.4 mM diethanolamine, pH 10. The substrate solution was applied as an even coat on the membrane.

In this example, the membranes were imaged outside the chamber, thus membranes were then placed on glass plates and wrapped with transparent plastic film. Fluorescence emission was excited by a 458 nm line of an argon ion laser (Lexel model 96) for 5MFP and BBTP or a long wave UV mercury lamp for MUFP. Laser light was passed through a lens to widen the beam distribution and through a 450 nm, 40 nm bandwidth bandpass filter (Melles Griot). Images were obtained by a cryogenically cooled CH210 CCD camera (Photometrics Ltd., Tucson, Ariz.) equipped with a 384×576 pixel TH7882 (Thomson CSF) CCD array and a 50 mm f/1.2 Pentax camera lens stopped down to f/22. Images were collected either through a 450 nm, 40 nm bandwidth bandpass filter (Melles Griot) (MUFP), a 3 mm OG515 (Schott) color filter (5MFP), or a 560 nm, 10 nm bandwidth bandpass filter (Oriel) (BBTP). Full length scans (approximately 24 inches) of the sequence ladders were obtained using TDI mode, which is described in detail below. During scanning, the blot was moved perpendicularly to the camera on a translation stage consisting of a Model 506241S rail table, MD series drive, and a MC3000 controller unit (DAEDAL Inc., Harrison City, Pa.). Two sets of lanes were acquired at 150 dots per inch in 8 minutes of scan time. Image data were downloaded from the camera controller frame buffer to a 286 PC-AT microcomputer, transferred to a Macintosh Quandra for conversion to a TIFF file and lane-finding, and then to a DEC 5000 workstation for base-calling and sequence analysis, described in detail below.

Figure 1A:
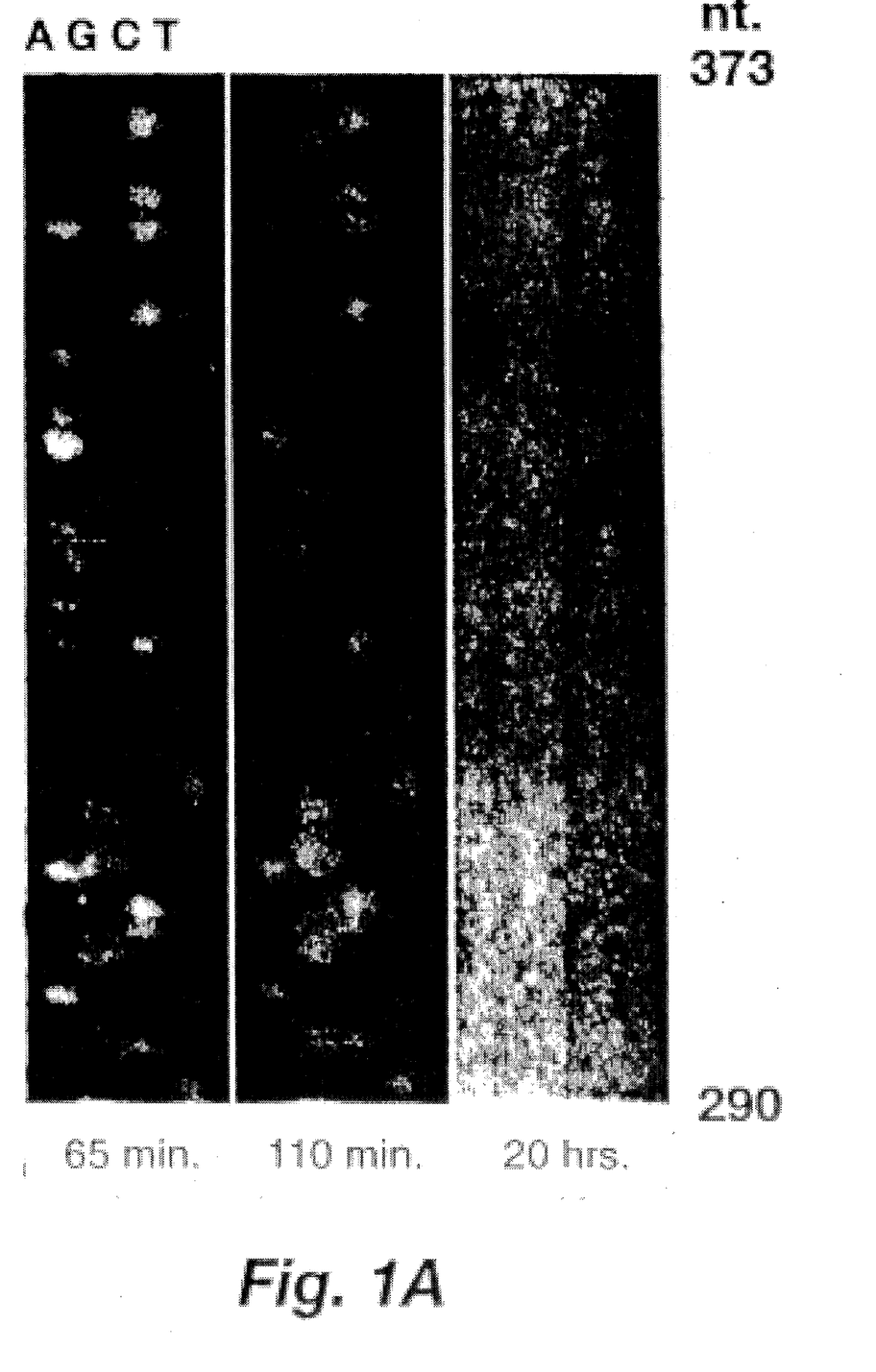
FIG. 1A shows a portion of a sequencing membrane corresponding to nucleotides 290–373 from the sequencing primer at 65 minutes, 110 minutes, and 20 hours after addition of the fluorogenic substrate MUFP.
Figure 1B:
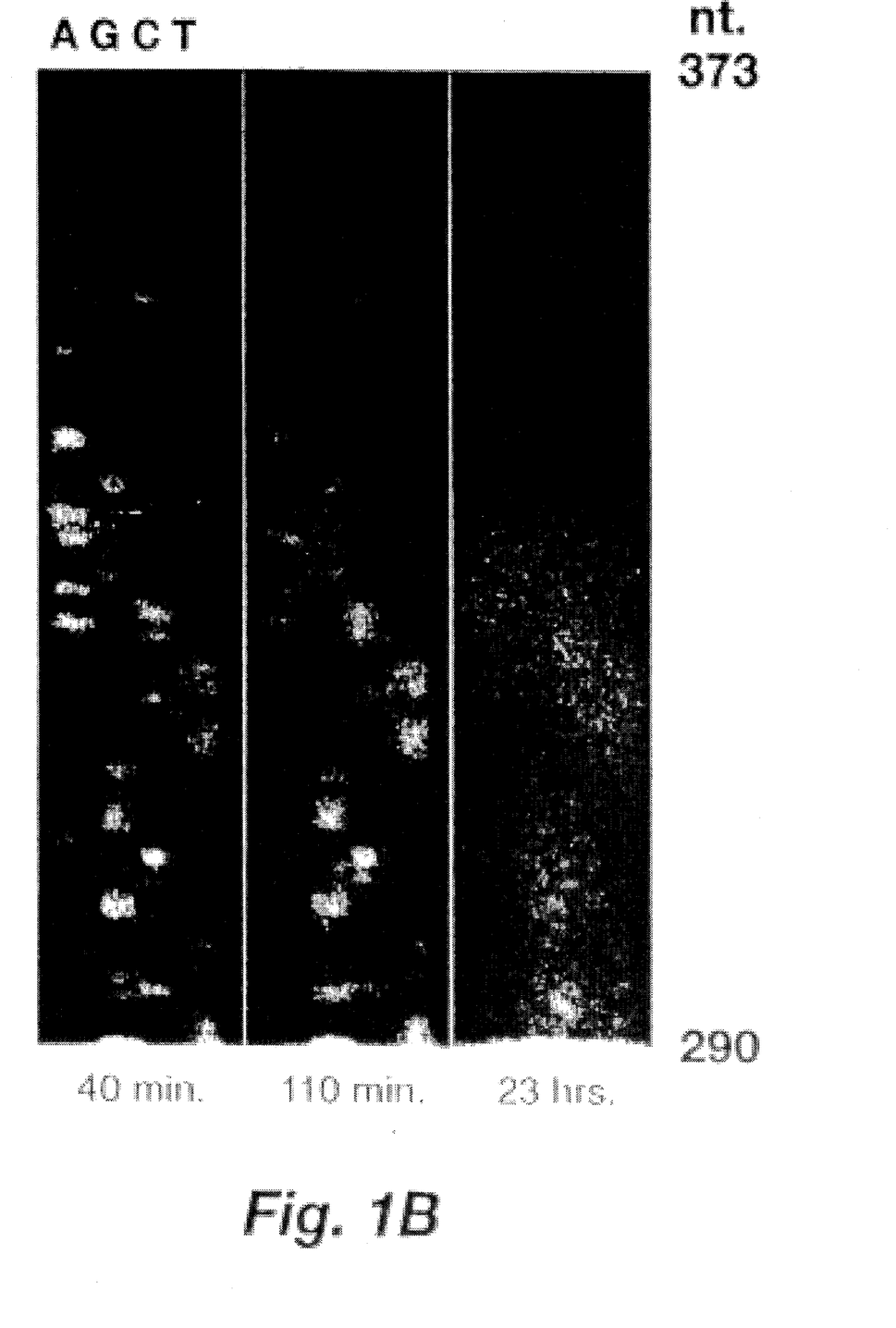
FIG. 1B shows a portion of a sequencing membrane corresponding to nucleotides 290–373 from the sequencing primer at 40 minutes, 110 minutes, and 23 hours after addition of the fluorogenic substrate 5MFP.

In all three cases, sequencing bands were visible to the eye upon illumination within 15 minutes of substrate application. With both MUFP and 5MFP, however, the sequencing ladders, though apparent, were visibly blurred (FIGS. 1A and 1B) even at early time points (65 and 40 minutes, respectively). The blurring is thought to be due to diffusion or bulk flow of the fluorescent product, or both. In contrast, BBTP yielded a relatively sharp ladder, FIG. 1C. Even after prolonged incubation to 20 hours, the sequencing ladder developed with BBTP could be read clearly. It is thought that the fluorescent product, BBT, interacts with the nylon membrane, perhaps through a simple hydrophobic interaction, to inhibit mobility. This property of BBTP, i.e. spatial localization, makes it clearly the most preferable of the substrates tested for sequence determination. MUFP and 5MFP appear to provide sufficient fluorescent product upon dephosphorylation by alkaline phosphatase to be useful for sequencing applications if a method of spatially localizing the fluorescent product could be developed. Similarly, other fluorogenic substrates than the three tested and described here could be used provided the fluorescent product could be bound to the membrane to yield sharply defined bands. The large quantities of light emitted using BBTP as substrate are easily imaged. Further, the fluorescent product, BBT, can be removed from the membrane by washing with detergent, thus making subsequent probing feasible. In this instance, BBT was removed from the membrane by five washes in 5% SDS, 125 mM NaCl, 25 mM sodium phosphate, pH 7.2, for five minutes each at 50° C. Other detergents and wash conditions may be suitable, also.

One of the advantages of generating blots from DNA sequencing gels from run-time transfer to the membrane is the constant band-to-band spacing seen on these blots. The position of sequencing bands on direct transfer electrophoresis blots is approximately linearly related to fragment length. Deviations may occur due to compressions, the inverse wedge profile of the gel, and long term drift in blotting speed. In direct transfer electrophoresis, the band spacing on the membrane, $\Delta S_{membrane}$, is proportional to the blotting speed, $v_{blotting}$, and to the ratio of the band spacing on the gel, $\Delta S_{gel}$, to the migration velocity, $v_{migration}$. This ratio is equal to the time interval between the elution of two adjacent bands, which is approximately constant over a wide range of fragments covering most of the separated sequencing fragments.

$$\Delta S_{membrane} = \frac{\Delta S_{gel}}{v_{migration}} v_{blotting}$$

Direct transfer electrophoresis gives the operator control over the band spacing on the membrane by choosing the appropriate membrane velocity, which is an important feature in the case of subsequent CCD based imaging. It is important to note that while the operator can increase the interband spacing in direct transfer electrophoresis by increasing the blotting speed, the electrophoretic resolution is not improved by this process. Loss of band resolution due to the limited resolution of the imaging optics is easily prevented by using direct transfer electrophoresis.

Automated Imaging Hybridization Chamber

The automated imaging hybridization chamber is an integrated system for automatically performing hybridization of nucleic acid probes to membrane-bound target nucleic acids under controlled conditions. When certain fluorescent probes are used, such as the enzyme-linked probe system using BBTP described above, an image of the nucleic acid on the membrane can be obtained via the transparent window in the outer cylinder without removing the membrane from the chamber compartment. While the chamber system described herein is not limited to a single hybridization chemistry, it was configured specifically for the use of fluorescent probe systems. It was designed, however, to be flexible enough to permit use with other systems. Other probes, such as radioactive probes, could be used in connection with this chamber, but would not utilize the advantage of imaging with the membrane in the chamber. Further, although the hybridization chamber system was designed specifically for sequencing applications, it is capable of handling other membrane-based detection applications such as colony and plaque hybridizations; Southern, Northern and Western blot procedures; multiplex genotyping of simple sequence repeats; sequencing and mapping by hybridization; and dot, slot, and allele-specific oligonucleotide blot techniques. All of the functions of the chamber system are computer controlled and fully definable by the user. The geometry of the chamber device is dictated by a need for the smallest workable fluid volume, for small air volume, to image the pattern of nucleic acid on the membrane, and for accurate temperature control (±2° C.).

Figure 2:
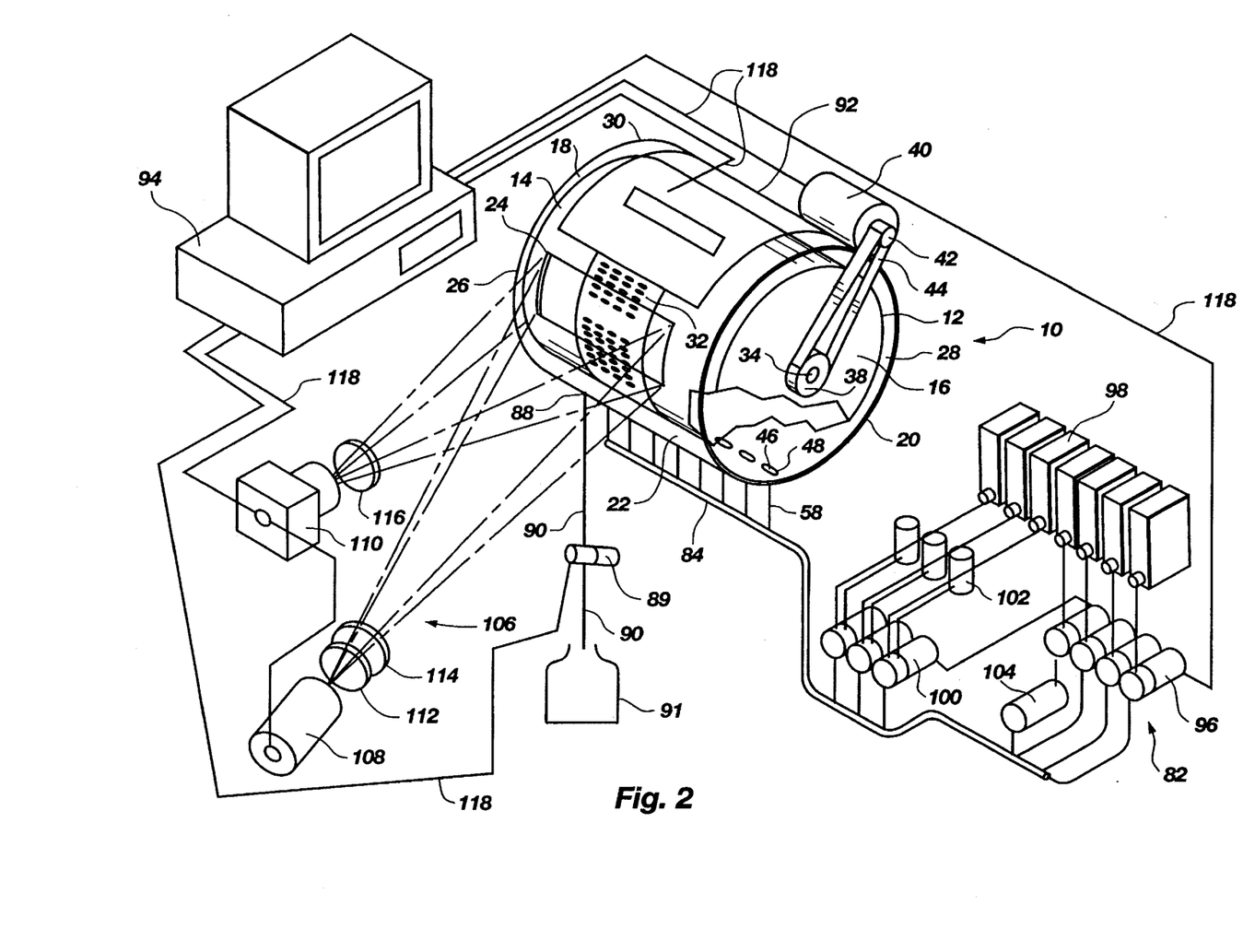
FIG. 2 is a schematic perspective view of the automated imaging hybridization chamber system according to the present invention.

Referring now to FIG. 2, the chamber device 10 contains two concentric nested horizontal cylinders, an inner sealed cylinder 12 having a continuous cylindrical sidewall 14 and sealed ends 16 and 18, and an outer cylinder 20 having a cylindrical sidewall 22 containing a visible light transparent window 24 and entry means 26 for gaining access to the exterior surface of the sidewall 14 of the inner drum. The end 28 of outer cylinder 20 is also sealed, whereas end 30 can also constitute the entry means 26, in which case end 30 is sealable with an "O" ring positioned between end 30 and sidewall 22. Inner cylinder 12 is removable from outer cylinder 20 through the entry means 26. The membrane 32 containing bound nucleic acid to be hybridized is mounted on the exterior surface of the sidewall 14 of the inner cylinder 12 with stainless steel wire bails (not shown). The inner cylinder 12 is rotatable on an axle 34 such that there is a small clearance (e.g., 0.125 inch) between the outside surface of the sidewall 14 of rotatable inner cylinder 12 and the inside surface of the sidewall 22 of stationary outer cylinder 20. The space 36 between these drum surfaces is referred to as the "chamber compartment." The clearance between the respective sidewalls of the inner and outer cylinders that defines the chamber compartment 36 should be of sufficient width that the inner cylinder 12 can rotate within the outer cylinder 20 without the membrane 32 coming in contact with the interior surface of the outer cylinder sidewall 22. Disposed on one end of the axle 34 is a driven gear wheel 38. The mechanism for rotating the inner cylinder 12 includes a stepper motor 40 which may be disposed on the outside of the outer cylinder 20 or another stationary object such as a table or machine chassis (not shown). Coupled to the stepper motor 40 is a driving gear wheel 42. The driving gear wheel 42 is coupled by a toothed belt 44 to the driven gear wheel 38 mounted on the axle 34. Thus, when the stepper motor 40 causes the driving gear wheel 42 to rotate, the belt 44 is caused to rotate the driven gear wheel 38, which in turn rotates the inner cylinder 12 within the outer cylinder 20.

Figure 3:
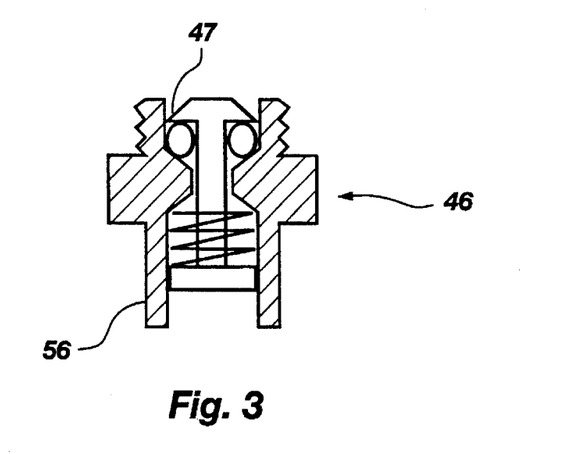
FIG. 3 shows an enlarged cross sectional view of an illustrative check valve contained in the automated imaging hybridization chamber shown in FIG. 2.
Figure 4:
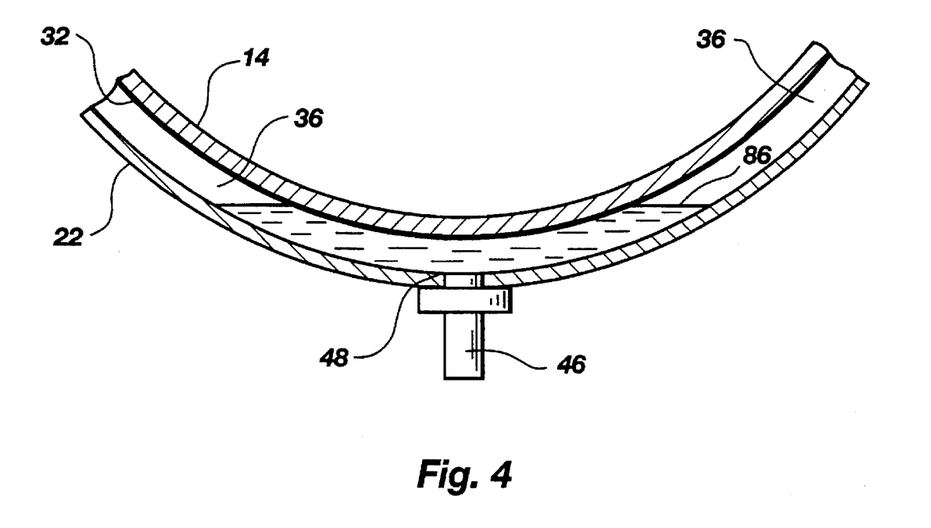
FIG. 4 shows an end sectional view of a portion of the automated imaging hybridization chamber shown in FIG. 2 taken along lines 4—4 of FIG. 2.

The hybridization process requires various fluids to be brought into contact with the membrane 32 in the lower portion of chamber compartment 36 and then to be removed by drainage from the chamber compartment 36 and replaced by other fluids introduced into the chamber compartment 36. It is crucial that each fluid in the chamber compartment 36 be kept pure and uncontaminated by other fluids. The various fluids are added to or removed from the chamber compartment 36 through a number of valves 46 contained in ports 48 drilled in the bottom of the cylinder 20. Into each port 48 is threaded a fluid tight spring loaded check valve 46 assembly, FIG. 3. These valves 46 can be actuated by fluid pressure from pumps that deliver the solutions to the chamber compartment 36, by means of solenoids, or the like. The configuration of the valve assemblies 46 with minimal space 47 (FIG. 3) for holding liquid on the chamber side of the valve when the valve is closed is very significant because of the importance of minimizing the volume of liquid that would be available to contaminate a subsequent step of the process. One embodiment of the chamber device 10 contains 20 such ports 48 with associated valve assemblies 46; however, the number of ports 48 and valve assemblies 46 is variable. The valve assembly 46 in each port 48 is connected, via a hose connection end 56 of valve assembly 46, to a hose 58 extending from a fluid delivery module 82, which will be described in more detail momentarily. The hoses 58 connecting fluid delivery modules 82 with valve assemblies 46 contained in the various ports 48 have no fluid connection with one another, but may be gathered together in a hose bundle 84 for convenience. The ports 48 are placed in the bottom of the horizontal outer cylinder 20 because it is important for minimizing contamination of succeeding steps in the process that they be located within the fluid puddle 86 (FIG. 4) that accumulates in the lower portion of the chamber compartment 36 when fluid is pumped into the chamber compartment 36 through the valve assemblies 46 contained in outer cylinder 20. This allows subsequent wash steps to cleanse space 47 in the same way and in the same order that the membrane is treated. As shown in FIG. 4, the volume of the fluid puddle 86 is sufficient to contact the membrane 32 secured to the exterior surface of the sidewall 14 of the inner cylinder 12 when the inner cylinder 12 is rotated. Further, the dead volume in the chamber compartment 36 above the check valve assemblies 46 must be kept to a minimum so that the residue from the previous solution is removed in a succeeding washing step and for minimizing the expense connected with the various liquids. One or more ports 48 serve as drains and contain drain valves 88 configured in any suitable manner so as to be operated manually or automatically under computer control. When drain valves 88 are opened, a drain pump 89 pumps spent fluid out of the outer cylinder 20 through drain hoses or lines 90 to a drain reservoir 91. Pneumatic jacks (not shown) assist draining by tilting the chamber device 10 to a position about 5° from horizontal so that the spent fluid accumulates over the drain valves 88, which are advantageously located near an end of the outer cylinder 20. After draining is completed, the pneumatic jacks return the chamber device 10 a horizontal position.

Mounted on the outside and covering the circumference of the cylindrical sidewall of horizontal outer cylinder 20, excluding the area occupied by window 24 and any entry means if these are different from the window 24, is an adhesive film heating element 92 for controlling the temperature of the fluids in the chamber compartment 36 and hence the temperature of the environment of the membrane. A thermocouple (not shown) is mounted on the inner surface of the outer cylinder 20 in chamber compartment 36 for monitoring the temperature of the chamber compartment 36 so that the temperature may be regulated as needed by proportional control of the heating element 92. The heating element 92 and thermocouple are connected to a computer 94 to provide continuous monitoring and regulation of the temperature. Further description of computer control of the chamber device 10 will be provided momentarily. The outer cylinder 20 has ends 28 and 30 which make the chamber device 10 virtually airtight so that evaporation or other loss of fluid from the chamber device 10 is minimized during hybridization cycles that may last 12 hours. The small volumes of fluid utilized in making up the fluid puddle 86, e.g., about 50–100 ml in one embodiment of the chamber device 10, are particularly susceptible to even small amounts of fluid loss, especially at elevated temperatures.

The fluid delivery modules 82 can be made in any suitable form; two forms are illustrated in FIG. 2. The simplest is a conventional metering pump 96 that delivers the larger volumes of relatively inexpensive wash solutions used for washing the membrane 32. These relatively inexpensive solutions are stored in large volume reservoirs 98. The more complex type of module involves a double-headed peristaltic pump 100, wherein each head is coupled to the same motor but has a different displacement. This configuration allows the fluid delivery module 82 to mix a relatively small volume of concentrated solution of more expensive and sometimes perishable probe with other solutions. These concentrated fluids are stored in probe concentrate reservoirs 102 until use, and the other solutions are stored in large volume reservoirs 98. In the event that fluids containing perishable components are used, a solid state, proportional control refrigeration unit (not shown) may be coupled to the system for preserving the perishable components from degradation. Certain fluids, for example wash solutions, are more effective at elevated temperatures than at room temperature. These fluids may be heated inside the chamber compartment 36 by the heating element 92. However, this method of heating the solutions causes a time delay that is multiplied by the number of solutions heated. This time delay can be eliminated by preheating the fluids with a proportional control batch heater 104 installed in the fluid path for heating the fluids just prior to their entry into chamber compartment 36.

The integrated imaging system also advantageously contains an imaging assembly 106 for obtaining an image of the pattern of hybridization to membrane-bound nucleic acid while the membrane 32 is within the chamber compartment 36. The sidewall 22 of outer cylinder 20 contains a window 24 of optically transparent material through which the membrane 32 mounted on the exterior surface of the sidewall 14 of inner 12 may be visualized. A suitable material for the window 24 is LEXAN, although other materials may function equally well. The window 24 may become fogged by condensation within the chamber compartment 36, however the heating element 92 defogs the window 24. Optionally, an interior wiper (not shown) can be used to defog the window 24. The imaging apparatus assembly 106 includes a light source 108, such as a laser or a tungsten-halogen lamp with an appropriate band pass filter, tailored to the absorption wavelength of the fluorescent marker and a CCD camera 110 with filter for recording the image. The light source 108 is placed an appropriate distance from the chamber device 10 and pointed so that the monochromatic light emitted by the light source 108 passes through the window 24 and illuminates the membrane 32. The fluorescent marker on the membrane 32 is excited by the incident light and emits a fluorescent signal at a characteristic wavelength for the particular fluorescent marker. The fluorescent signal is detectable by the CCD camera 110 placed in a suitable location for observing the emitted fluorescence. Both the light source 108 and the CCD camera 110 are connected to the computer 94 for controlling their operation and storing the data that are collected by the CCD camera 110. Focusing and filtering optics are included in the imaging apparatus 106 for widening the beam distribution and filtering unwanted wavelengths from both the incident light and the fluorescent signal. As shown in FIG. 2, these focusing and filtering optics can include a water-cooled infrared filter 112 and excitation bandpass filter 114 combined with the light source 108 for illuminating the membrane 32, and an emission bandpass filter 116 combined with the CCD camera 110 for removing unwanted background fluorescence and light from the excitation light source 108. Computer control cables 118 connect the computer 94 to each element of the system that is computer controlled: heating element 92, stepper motor 40, metering pump 96, dual head peristaltic pump 100, drain pump 89, light source 108, CCD camera 110, and pneumatic jacks (not shown).

Imaging with CCD Camera

The full image of fluorescent signals being emitted from a 36×12 inch membrane upon appropriate illumination can be acquired within about 1.5 minutes with a CCD camera operating in TDI mode. Fluorescent images are acquired by a CL-E1-2048-S CCD camera (DALSA Inc., Waterloo, Ontario, Canada) equipped with a 2048×96 pixel IL-E1-2048 TDI array (DALSA). The camera housing is mated to a custom fabricated peltier cooling system, which cools the camera to 0° C. during scanning operations. The analog output of the CCD camera is digitized and written to disk using an AT-MIO-16F-5 Multifunction I/O board, which is mounted in a 486 PC-AT computer. Intermediate to the CCD camera and the I/O board is a custom designed interface board, which provides compatibility between the camera and the I/O board. Also, the I/O board can generate a trigger signal that is used to shift CCD pixel rows for TDI scanning. A f/1.4 50-mm focal-length Nikon photographic lens is mounted on the camera, and fluorescing membranes are imaged at an approximate distance of 29.5 inches from the lens for 150 dots per inch (dpi) resolution or at about 17 inches for 300 dpi resolution. When generating an image, the membrane mounted to the rotating inner cylinder of the hybridization device is moved across the camera's field of view.

An area CCD array is composed of two major functional components, a parallel register consisting of a two-dimensional array of light-sensitive CCD elements, and a single-line linear output register, positioned along one side of the parallel register and connected to an on-chip amplifier. Photons striking the CCD surface generate photoelectrons, which are trapped in the CCD element nearest to the location of photon incidence. After the array has been exposed to light, readout of the photogenerated charge is performed by simultaneously shifting charge packets of all lines in parallel toward the output register. Having arrived in the output register, the charge packets are shifted one by one in the perpendicular direction toward the on-chip amplifier and subsequent analog to digital conversion.

When a CCD snapshot is acquired, all photogenerated charge packets are read out in an uninterrupted series of parallel transfers followed by serial transfers and digitization after the shutter has closed. No charge transfer takes place during exposure. In TDI mode, in contrast, the parallel shifting of the charge toward the output register is under the control of an external trigger, the TDI trigger. The parallel transfer is delayed until the arrival of a pulse on the time delay trigger line. The controlled transfer of charge is used while the photoactive area is exposed to light and the accumulation of photogenerated charge takes place. A line in the resulting TDI image represents light from a line in the object plane that is scanned across the field of view of the camera. This is made possible by synchronizing the image scan speed and the trigger signal, which controls the pixel migration speed. The major advantage of using the TDI mode (also true for line scan mode) is that the number of scan lines is not limited to the number of lines of the parallel register as in standard full-frame operation. The limitations on the length of the TDI scan are determined by the maximum size of the digital storage space, which can be a computer hard disk. A further advantage of TDI mode is its ability to average differences in CCD pixels. Each element of an image is the result of the incremental charge accumulations in the TDI pixels when the image element coincided therewith.

A TDI scan offers increased sensitivity per unit time when compared to a line scanner equipped with a linear array, because the light is collected simultaneously on the entire photoactive surface of the CCD. Because the sensitivity of a cooled CCD in low-light-level measurements is approximately proportional to the size of the photoactive area, the sensitivity of an area CCD operated in TDI mode is increased over the sensitivity of a linear array consisting of the same time elements approximately by the number of scan lines that are simultaneously monitored. W. Washkurak et al., CCD Image Sensors 198–201 (DALSA Inc., Waterloo, ON, Canada, 1988).

Automated Gel Reading Software

An automated sequence reader is used to convert the digital signals acquired by the CCD camera comprising the pattern of fluorescence from the sequencing membrane into a called sequence of nucleotides. The sequence reader used in connection with the automated multiplex sequencing system disclosed herein was a base-calling algorithm described in commonly assigned copending patent application Ser. No. 07/978,915, filed Nov. 19, 1992, entitled METHODS AND APPARATUS FOR ANALYSIS OF CHROMATOGRAPHIC MIGRATION PATTERNS, and hereby incorporated by reference. Other automated sequence readers are commercially available and could be used in the presently described system, such as those by ABI, Pharmacia, Milligen, Hitachi, and LiCor.

Example 4

Figure 1C:
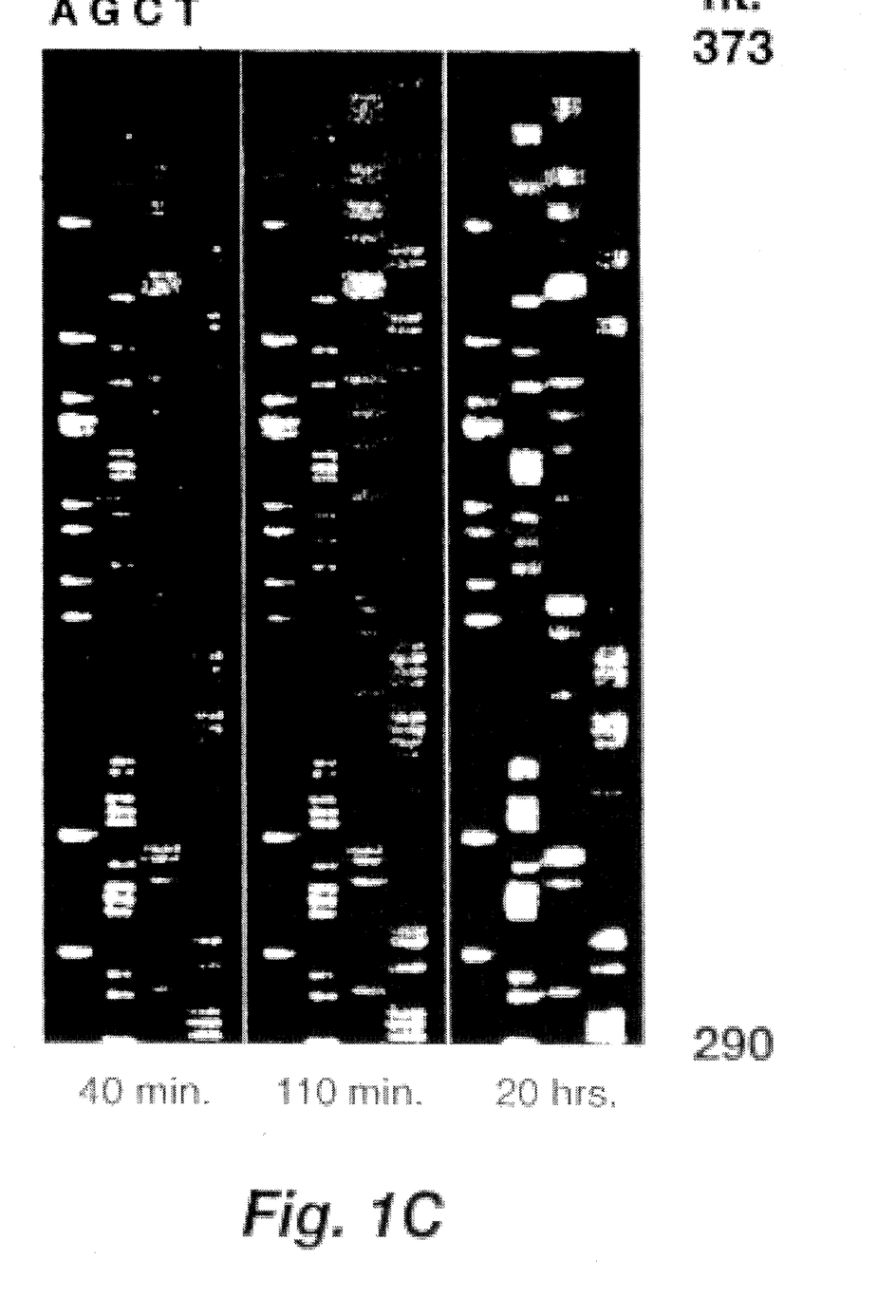
FIG. 1C shows a portion of a sequencing membrane corresponding to nucleotides 290–373 from the sequencing primer at 40 minutes, 110 minutes, and 20 hours after addition of the fluorogenic substrate BBTP.
Figure 5:
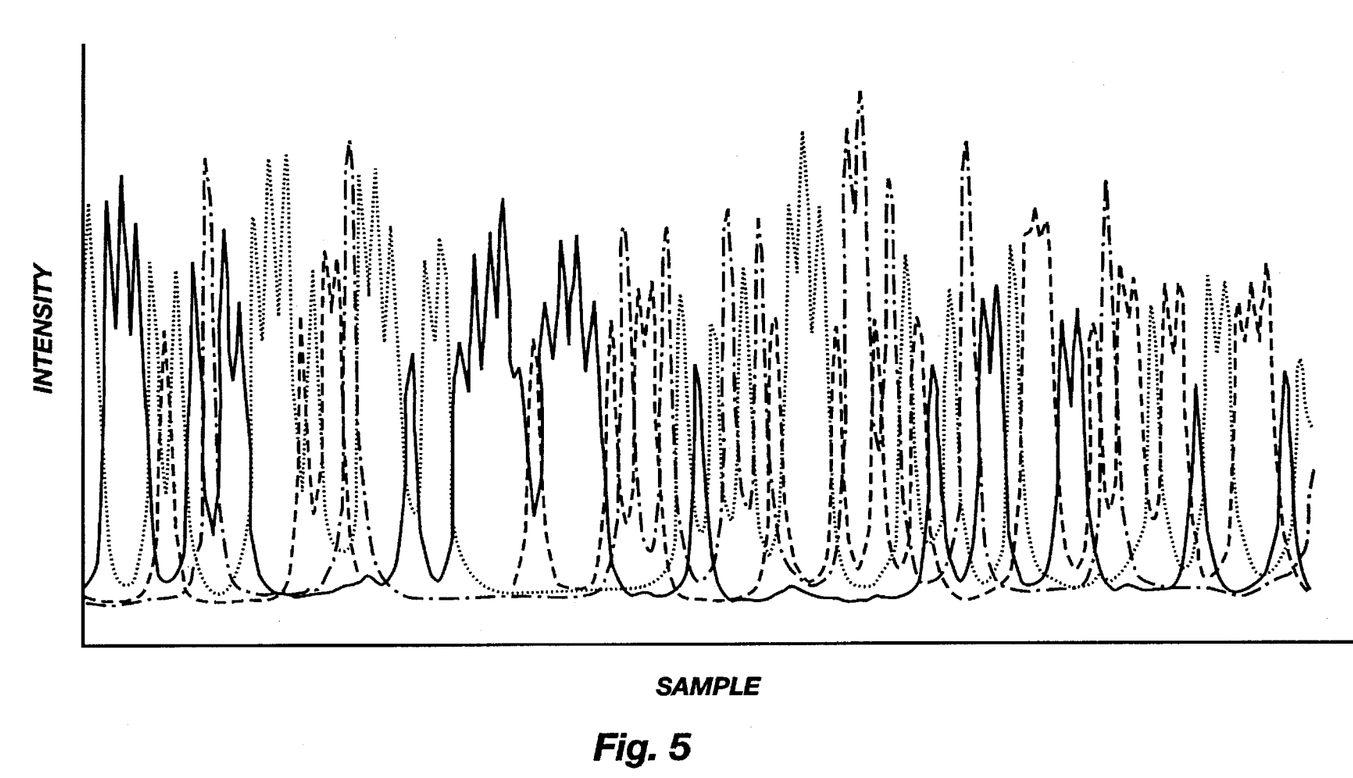
FIG. 5 shows a plot of unprocessed one-dimensional traces of a portion of a sequencing membrane read according to the present invention. The line patterns represent the four deoxynucleotides: T (solid), C (dashed), G (dotted), and A (dash-dot).

A full length image of the BBTP membrane, 40 minutes after addition of substrate, shown in FIG. 1C was acquired with a CCD camera operating in TDI mode and was processed using the automatic gel reading software of Ser. No. 07/978,915 modified to accept a positive fluorescent image rather than a negative one as is usual with imaging on X-ray film. FIG. 5 shows a portion of the unprocessed one-dimensional traces, obtained by averaging horizontally across several pixels at the lane centers. The BBTP membrane was up-sampled by a factor of two to produce a 300 dots-per-inch image expected by the gel reader. Lanes were found manually using a Macintosh program, and the data shown were produced by averaging the value of 15 pixels per row around the lane centers. The individual traces have not been processed in FIG. 5, but the traces have been slightly shifted relative to one another to obtain better alignment.

The automated reader yielded reasonably accurate sequence as far as the membrane was imaged, 653 nucleotides from the primer. There were 8 total errors (7 deletions and one substitution) in the 581 nucleotides deciphered, for an error rate of 1.4%. The first error occurred 381 nucleotides from the primer. Four of the eight errors occurred within the last 39 nucleotides and two of the remaining errors were due to compression and false stop artifacts.

Utility

Example 5

The utility of the automated multiplex sequencing system was shown by sequencing a 10.5 kb plasmid subclone of the human neurofibromatosis I genomic locus. Template DNA was prepared from a mapped set of 480-nucleotide sequencing transposon inserts. The transposon carries a NotI site, used for mapping and biotinylation, and two multiplex priming sites, one at each end of the element. Plasmid DNA (1 pmol) from each template was prepared by the alkaline lysis method, J. Sambrook et al., Molecular Cloning: A Laboratory Manual 1.25 (2d ed., 1989), which is hereby incorporated by reference. Then, the DNA was digested with NotI according to the instructions of the manufacturer, and the NotI site was filled in with bio-11-dCTP (Enzo Diagnostics) using the Klenow fragment of E. coli DNA polymerase I. Next the DNA was digested with EcoRI at sites flanking the inserted DNA and the biotinylated insert DNA was bound to 0.5 mg of M280 streptavidin dynabeads (Dynal, Glen Cove, N.Y.). The bead-bound DNA was then converted to single-stranded template by denaturation with 0.2N NaOH and the template was subjected to a sequencing reaction as described above except that a magnet was used to concentrate the bound DNA after the reactions were terminated. Dynabeads have an iron component that permits magnetic concentration of the beads and the bound DNA. Sequencing reaction products were loaded on a 4% polyacrylamide gel and subjected to electrophoresis as described in Example 1. Fractionated DNA fragments were directly transferred to a nylon membrane using the custom direct transfer apparatus described above. The membrane was removed from the apparatus, rehydrated in 40 mM sodium phosphate buffer, pH 7.6, and irradiated with a total of 225 mJ/cm$^2$ of UV light to cross link the DNA fragments to the nylon membrane. Unbound DNA was removed by washing the membrane in PBS (40 mM sodium phosphate, pH 7.6, 150 mM NaCl), 5% SDS, and then the membrane was placed in the automated imaging hybridization chamber. The controller was programmed for automatic operation and the steps described below proceeded automatically in a cycle time of 4.5 hours.

Hybridization of a probe specific for one of the two multiplex priming sites was begun by injecting 50 ml of prehybridization buffer (PBS+5% SDS) into the chamber compartment by means of the fluid delivery module. The rotation of the inner cylinder was set to sweep a bead of fluid across the concave surface of the membrane at approximately 20 second intervals. Pre-hybridization was at 50° C. for 30 minutes. Then, the 24-mer oligonucleotide probe was injected to a concentration of 25 pmol/ml. The probe was 3' end labeled with digoxigenin-11-dUTP and dATP in a 1:10 ratio. Hybridization was carried out for 120 minutes. Then, the hybridization buffer was removed by automatic opening of a drain valve and draining through a drain hose. The drain valve was closed and then wash buffer (PBS+5% SDS) was injected into the chamber by the fluid delivery module. Unhybridized probe was removed by 8 washes, each in 100 ml of wash buffer for 5 minutes at 50° C. Between washes, the wash buffer was drained by opening of a drain valve and draining through a drain hose, and then the drain valve was closed. After removal of the unhybridized probe was completed, a 1/5000 dilution of anti-digoxigenin antibody-alkaline phosphatase conjugate (Boehringer Mannheim) was injected into the chamber compartment by the fluid delivery module in a total volume of 40 ml of PBS containing 5% SDS and was allowed to bind to the digoxigenin-derivatized probe for 45 minutes at 24° C. Then, the conjugate solution was drained and unbound conjugate was removed by 1 wash with PBS, 5% SDS; 1 wash with PBS, 1% SDS; 3 washes with PBS; and 3 washes with 0.1M diethanolamine, pH 10.0, 1 mM MgCl$_2$, 0.01% sodium azide.

The alkaline phosphatase reaction was begun by draining the last wash solution and then adding 50 ml of BBTP solution (6 mg/ml in 2.4 mM diethanolamine, pH 9.0). After 180 minutes, fluorescence emission was excited by the 458 nm line of an argon ion laser (Lexel Model 96). The laser beam was passed through a lens to widen beam distribution and through a 450 nm, 40 nm band width, bandpass filter (Melles Griot). Images were obtained with a cryogenically cooled CH210 CCD camera (Photometrics), equipped with a 384×576 pixel TH7882 (Thomson) CCD array and a 50 mm f/1.2 Pentax camera lens stopped down to f/22. Images were collected through a 560 nm, 10 nm bandwidth, bandpass filter (Oriel). Full length scans of the sequence ladders were obtained in TDI mode. During scanning, the membrane was moved perpendicularly to the camera by synchronized movement of a stepper motor-driven translation stage to which the membrane was mounted, as controlled by the computer controller. Two lane sets were acquired at 150 dots per inch in 8 minutes of scan time. Image data were transferred to a Macintosh Quadra for conversion to a TIFF file and lane-finding, and then to a DEC 5000 workstation for base-calling and sequence analysis.

After acquisition of the data from probing with the first probe, the fluorescent product generated from the first probing was easily removed by a brief detergent wash consisting of five washes for 5 minutes each in PBS containing 5% SDS at 50° C. The steps of hybridization, binding of the enzyme conjugate, enzyme reaction, and data acquisition were repeated with a second probe. The membrane contained 10 sets of sequencing lanes, each of which contained a two-fold multiplexed sequence ladder. Two probings of this membrane generated sequence ladders from 18 of the sets of lanes, yielding 5841 nucleotides, or an average of about 325 nucleotides per set. The membrane was then subjected to a third round of hybridization using the probe used in the first hybridization, and ladders corresponding to the initial probing were reacquired with comparable quality.

Example 6

The same procedure is used as in Example 5 with the exception that images are obtained with a peltier cooled DALSA CL-E1-2048-S CCD camera equipped with a DALSA 2048×96 pixel IL-E 1-2048 array connected to a 486 PC-AT computer via an AT-MIO-16F-5 National Instruments board that converts the camera's analog signal to digital and writes the data directly to disk. Further, the membrane remains mounted on the inner cylinder of the chamber device and the membrane is moved perpendicularly to the camera by synchronized movement of the inner cylinder by the stepper motor, as controlled by the computer controller. Full length images are acquired in 1.5 minutes of scan time.

Example 7

Figure 6:
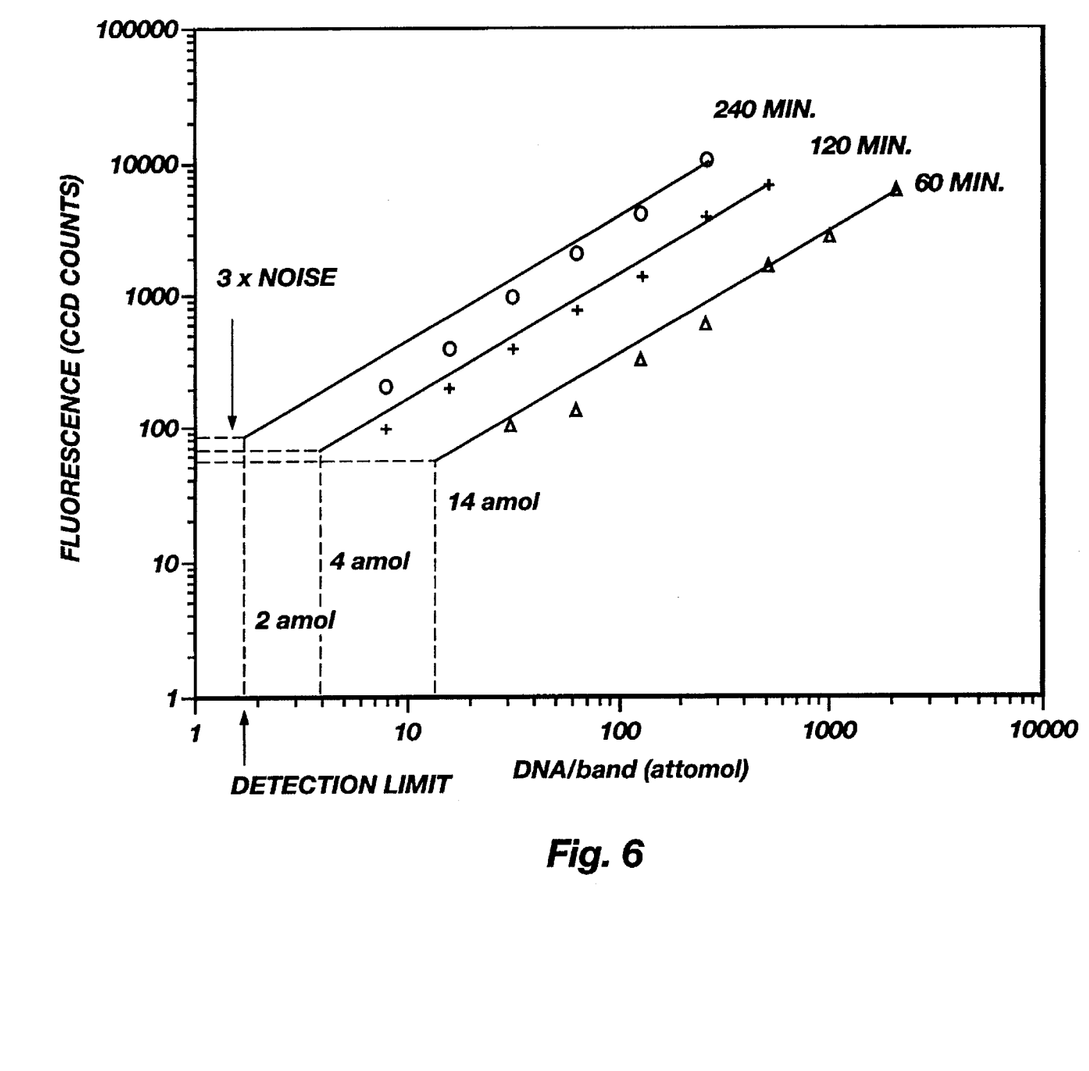
FIG. 6 shows the detection limit of a membrane-bound 75-mer oligonucleotide in a single direct transfer electrophoresis sequence band wherein the 75-mer oligonucleotide was probed with a complementary 25-mer oligonucleotide labeled with a single 5' biotin and detected with streptavidin-alkaline phosphatase and BBTP.
Figure 7:
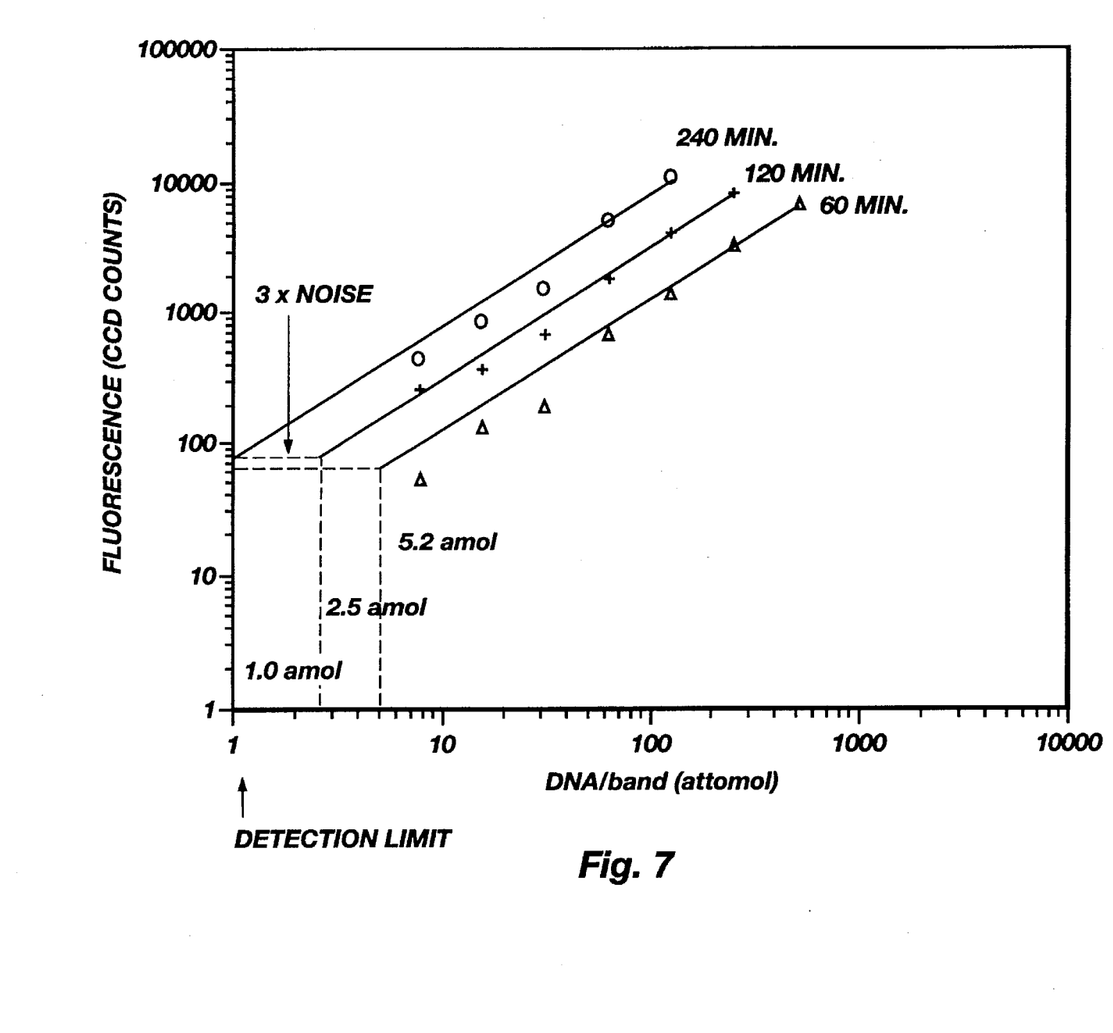
FIG. 7 shows the detection limit of a membrane-bound 75-mer oligonucleotide in a single direct transfer electrophoresis sequence band wherein the 75-mer oligonucleotide was labeled directly with a single 5' biotin and detected with streptavidinalkaline phosphatase and BBTP.

The sensitivity, detection limits, and efficiency of hybridization with the automatic multiplex sequence system was estimated as follows. A range of quantities of unlabeled and biotinylated 75-mer oligonucleotides were subjected to electrophoresis in a sequencing gel and then transferred to a membrane filter as described above. Unlabeled DNA was probed with a singly biotinylated oligonucleotide, but biotinylated DNA was not probed. The membrane was then exposed to streptavidinalkaline phosphatase conjugate, followed by addition of BBTP. The membrane was illuminated and imaged at three time points, as shown in FIGS. 6 and 7. Signal levels were approximately linear with time and quantity. Signal intensities were higher when biotinylated DNA was detected (FIG. 6) than when unlabeled DNA was later biotinylated and detected (FIG. 7). There was a two- to three-fold difference in intensity, presumably due to incomplete binding of the DNA to the membrane, effective loss of target DNA due to cross linking and steric factors, incomplete hybridization of biotinylated probe to bound target DNA, or combinations thereof. Limits of detection, defined as the quantity of DNA yielding a peak height equal to three times the standard deviation of the background, are calculated from least-squares estimates of the slopes of the lines. At 1 and 4 hours after application of the substrate, the limits of detection for a single biotin are 5 and 1 attomoles ($10^{-18}$ moles) for direct detection and 14 and 2 attomoles for a hybridized probe, respectively. Quantities of sequencing template in the 0.5 pmol range typically yield a few hundred attomoles of dideoxy-terminated chain per band. Thus, the technique described herein has the sensitivity required for low-level multiplexing (<10 reprobings), and the use of probes with multiple biotin molecules or the use of various amplification schemes should increase the signal further and allow for deep levels of multiplexing.

The background signal in these measurements consists of three components: intrinsic membrane fluorescence, substrate fluorescence, and fluorescence of product generated from non-specifically bound DNA or streptavidin-alkaline phosphatase or both. Initially, membrane fluorescence dominates the background signal, as determined by fluorescent measurements on membranes with and without substrate. At later times, fluorescent product due to non-specific enzyme binding can become the major background component. This same background limits enzyme-linked chemiluminescent detection measurements and is very sensitive to probing, wash conditions, and the physical handling of the membrane, as can be seen from its macroscopic inhomogeneity. Integration of automated probing and detection cycles, as well as alternate probing schemes, may help to minimize this type of background. The background signal due to membrane fluorescence could be decreased by the use of a low fluorescence membrane, T. Chu et al., 13 *Electrophoresis* 105 (1992); U.S. Pat. No. 5,112,736, or by the development of fluorogenic substrates whose products excite in the near-infrared, where intrinsic membrane fluorescence may be lessened. Any such change of materials would have to preserve the postulated membrane/product interaction, as well as low substrate fluorescence and low non-specific binding of the enzyme conjugate.

The fluorescent signal is greater than comparable chemiluminescent signals by a factor of more than $10^5$. The absolute intensity of the signal is more than sufficient for imaging. To avoid saturation of the CCD during TDI scanning of the sequence ladders, the camera lens was stopped down to f/22, which decreases the light intensity by a factor of 336 compared to the largest aperture, f/1.4, and neutral density filters were frequently required. Increase of the excitation light could increase the signal intensity further by several orders of magnitude. Even though the absolute signal intensity is sufficient for simple detection, increases in signal-to-noise ratio would still be desirable, and there may be much room for improvement. BBT was excited with 458 nm light because the argon laser was a convenient light source. BBT excites maximally near 430 nm, and the excitation peak is approximately twice the value of 458 nm, thus a two-fold improvement in sensitivity might be achieved by a change in excitation wavelength. While the details of emission filtering were not found to be extremely critical, a more careful optimization of the optics might be fruitful.

We claim:

1. A method for enzyme-linked fluorescence detection of nucleic acid comprising the steps of:

(a) attaching the nucleic acid to be detected to a nylon membrane;

(b) contacting the nylon membrane with an oligonucleotide probe containing a binding moiety for binding alkaline phosphatase and which is able to hybridize specifically with a complementary sequence on the nucleic acid, thereby hybridizing said probe to said nucleic acid;

(c) contacting the probe with alkaline phosphatase, thereby binding the alkaline phosphatase to said binding moiety on the probe;

(d) contacting the alkaline phosphatase with BBTP so that the alkaline phosphatase converts the BBTP into a fluorescent product, wherein the fluorescent product interacts with the nylon membrane and is spatially localized thereon; and (e) illuminating said fluorescent product with a beam of light capable of exciting fluorescence by said fluorescent product, thereby exciting fluorescence by said fluorescent product wherein said fluorescence produces a pattern that reflects the location of said nucleic acid on said membrane.

2. The method of claim 1 wherein step (c) further comprises, as a preliminary step, attaching to said alkaline phosphatase a bridging molecule for binding said binding moiety, said bridging molecule forming a bridge for binding of said alkaline phosphatase to said binding moiety.

3. The method of claim 2 wherein said binding moiety comprises a biotin molecule covalently attached to said probe and said bridging molecule is selected from the group consisting of streptavidin and avidin.

4. The method of claim 2 wherein said binding moiety comprises a digoxigenin molecule covalently attached to said probe and said bridging molecule comprises an anti-digoxigenin antibody.

5. The method of claim 2 further comprising (f) imaging said pattern by imaging means.

6. The method of claim 5 wherein said imaging means includes a light source for producing and delivering a beam of light of an appropriate wavelength to the nylon membrane for exciting fluorescence of said fluorescent product.

7. The method of claim 6 wherein said light source is selected from the group consisting of a laser and a tungsten-halogen lamp with a band pass filter.

8. The method of claim 6 wherein said imaging means further comprises a filter for removing undesirable wavelengths of light from said beam of light.

9. The method of claim 6 wherein said imaging means includes a CCD camera for recording an image of said fluorescence emanating from said fluorescent product on said nylon membrane and a filter for removing wavelengths of light from said fluorescence of said fluorescent product that interfere with recording said image.

10. The method of claim 9 wherein said CCD camera is operable in Time Delay and Integration mode.

* * * * *